US012702637B2

(12) United States Patent
Mathias et al.

(10) Patent No.: US 12,702,637 B2
(45) Date of Patent: Aug. 11, 2026

(54) TOPICAL COSMETIC COMPOSITION, USE OF THE COMPOSITION AND TONIC FOR FACIAL APPLICATION

(71) Applicant: Natura Cosméticos S.A., São Paulo (BR)

(72) Inventors: Michele Helena Mathias, Cajamar (BR); Camila Pereira Santos, Cajamar (BR); Luciana De Miranda Chaves Vasquez Pinto, Cajamar (BR); Silas Arandas Monteiro E Silva, Cajamar (BR); Joice Savietto, Cajamar (BR); Edjane Lima Gusmão, Cajamar (BR); Nicole Gregório Pinto, Cajamar (BR)

(73) Assignee: Natura Cosméticos S.A., São Paulo-SP (BR)

( * ) Notice: Subject to any disclaimer, the term of this patent is extended or adjusted under 35 U.S.C. 154(b) by 740 days.

(21) Appl. No.: 17/633,415

(22) PCT Filed: Aug. 6, 2019

(86) PCT No.: PCT/BR2019/050319

§ 371 (c)(1), (2) Date: Feb. 7, 2022

(87) PCT Pub. No.: WO2021/022345

PCT Pub. Date: Feb. 11, 2021

(65) Prior Publication Data

US 2022/0287953 A1 Sep. 15, 2022

(51) Int. Cl.

| | |
|---|---|
| ***A61K 8/9728*** | (2017.01) |
| ***A61K 8/368*** | (2006.01) |
| ***A61K 8/49*** | (2006.01) |
| ***A61Q 19/00*** | (2006.01) |

(52) U.S. Cl.

CPC ............ *A61K 8/9728* (2017.08); *A61K 8/368* (2013.01); *A61K 8/4913* (2013.01); *A61Q 19/008* (2013.01)

(58) Field of Classification Search

None

See application file for complete search history.

(56) References Cited

U.S. PATENT DOCUMENTS

| | | | | |
|---|---|---|---|---|
| 9,333,169 | B2 * | 5/2016 | Paufique | A61Q 19/00 |
| 9,629,856 | B2 | 4/2017 | Dreher | |
| 9,849,077 | B2 * | 12/2017 | Gan | A61K 8/42 |
| 2008/0069784 | A1 * | 3/2008 | Millikin | A61K 8/4913 514/23 |
| 2010/0015071 | A1 | 1/2010 | Park et al. | |
| 2012/0164121 | A1 | 6/2012 | Paufique | |
| 2015/0118165 | A1 | 4/2015 | Rudolph et al. | |

FOREIGN PATENT DOCUMENTS

| | | | |
|---|---|---|---|
| BR | PI0807326-0 | A2 | 2/2014 |
| BR | PI 1010479-8 | A2 | 9/2015 |
| CN | 105250189 | A | 1/2016 |
| WO | WO 95/03779 | A1 | 2/1995 |
| WO | WO 2006/014237 | A2 | 2/2006 |
| WO | WO 2011/027085 | A2 | 3/2011 |
| WO | WO 2013/167220 | A1 | 11/2013 |
| WO | WO 2014/094375 | A1 | 6/2014 |

OTHER PUBLICATIONS

Kristensen et al. Acta Derm Venereol (Stockh) 1991. 71, pp. 37-40.*

Bare Escentuals, Intensive Glow Pads Brightening Treatment, Mintel, 6 pgs., (May 2014).

Herbal Dynamics, Hyaluronic Acid & Oat Overnight Recovery Mask, Mintel, 6 pgs., (Sep. 2018).

Rohto Pharmaceutical, Cinnamon Mousse Foam Cleanser, Mintel, 2 pgs., (Jul. 2018).

Schaefer, Katie, "Detoxifying Aged Skin Cells," Cosmetics & Toiletries, 2 pgs., (Dec. 30, 2009).

International Searching Authority, International Search Report and Written Opinion received for International Application No. PCT/BR2019/050319, dated Mar. 30, 2020, 17 pages, National Institute of Industrial Property, Brazil.

* cited by examiner

*Primary Examiner* — Vera Afremova

(74) *Attorney, Agent, or Firm* — Alston & Bird LLP

(57) ABSTRACT

The present invention is a topical cosmetic composition that provides oiliness reduction and control, as well as pore size reduction, maintenance of the pH and the skin's natural and healthy microbiota. The present invention is within the field of cosmetic science, more precisely it concerns skin care preparations.

5 Claims, 3 Drawing Sheets

TOPICAL COSMETIC COMPOSITION, USE OF THE COMPOSITION AND TONIC FOR FACIAL APPLICATION

CROSS-REFERENCE TO RELATED APPLICATIONS

This application is a national stage filing of International Application PCT/BR2019/050319 filed on Aug. 6, 2019, which designated the U.S. and which is hereby incorporated herein in its entirety by reference.

FIELD OF THE INVENTION

The present invention describes a topical cosmetic composition that provides oiliness reduction and control, as well as pore size reduction, maintenance of the pH and the skin's natural and healthy microbiota. The present invention is within the field of cosmetic science, more precisely it concerns skin care preparations.

BACKGROUND OF THE INVENTION

Skin or integument is a double layered membrane that covers the entire body surface and is adjacent to mucous membranes that cover the human body orifices. It exhibits great variation in thickness along its entire length, ranging from 1 to 4 mm according to its required biological functions. Among these functions are maintenance of the body integrity by protecting the is body against injuries, absorbing and excreting liquids, regulating the body temperature, absorbing ultraviolet rays, metabolizing vitamin D, providing sensory stimuli and cosmetic functions.

The skin can be divided into two parts, the outermost layer being represented by the epidermis and the innermost layer being the dermis which rests on the subcutaneous cellular tissue, which is also part of the skin's structure.

The epidermis is formed by a keratinized stratified squamous epithelium that contains 4 layers: basal, spinous, granular and corneal (horny) layers.

The epidermis cells, in turn, can be divided into 4 groups: stem cells, proliferative cells, differentiated cells and functional cells. The epidermis also has dendritic cells (melanocytes and Langerhans cells) and neuroendocrine (Merkel) cells. Like every epithelium, the epidermis cells are renewed indefinitely thanks to a continuous mitotic activity.

The skin pH helps to maintain the skin protective mantle. pH is seen by some authors as an important functional skin indicator, being the result of lactic acid production, sebaceous secretion and sweat, giving the skin surface what is conventionally called "skin acid mantle".

The skin has a slightly acidic pH (4.6-5.8), which contributes to bactericidal and fungicidal protection on its surface. Also, cutaneous secretions have an appreciable buffering capacity. Skin pH is often changed as a result of the use of inappropriate topical products.

Changes in skin pH can cause irritation as well as favor bacterial colonization. Accordingly, cosmetic products must not modify the physiological characteristics of the region where they are applied.

Also, skin is covered by a lipid layer from sebum and epidermal lipids. Sebum is an important skin factor, as it can be classified according to the amount of sebum secreted. In the cosmetic field, the facial skin is usually classified as dry, normal, combination or oily skin.

There is a cosmetic concern related to oily skin, that is, skin that produces a large amount of sebum. This is because such a condition modulates skin aspects such as: intense shine, sticky feeling, tendency to acne, pimples and blackheads and dilated and irregular pores.

Sebum is a lipid mixture comprising triglycerides, fatty acid esters, esterified waxes, squalene and cholesterol esters. Its main function is to protect the skin by controlling transdermal water loss, forming a waterproof barrier.

The face has an average of three to nine hundred pilosebaceous follicles per square centimeter, however, several factors are involved in the regulation of the amount of sebum deposited on the skin surface, so what happens in the sebaceous gland should not be considered as the only cause of oiliness on the skin.

In people with oily skin, the sebaceous glands are hyperactivated, which can cause excessive shine and the presence of dilated pores. A consequence of dilated pores is an even more oily skin, with a greasy and shiny appearance.

A reduction in the pore diameter leads to a reduced amount of oil released and it further provides the skin with a healthier and blemish-free appearance.

Oiliness is still related to disturbances in the skin microbiota. This is because the microbiota has a variety of microorganisms that depend on the skin conditions. Where oiliness increases due to internal or external factors, the skin conditions favor bacteria that do not require oxygen to grow and use lipids instead. Such a population increases, reducing other bacterial populations that grow better in less oily environments. Thus, the inflammatory response that leads to the appearance of acne keeps the vicious circle of excessive oil and lipid-consuming bacteria, leaving the skin unbalanced.

Gram positive bacteria usually predominate in the skin, such as *Staphylococcus, Corynebacterium* and *Propionobacterium*. It interacts with other microbes, human cells and the immune system via different pathways that mediate the risk for diseases. Disturbances in this microbiota may influence the onset of diseases.

The state of the art describes a variety of cosmetic compositions. For example, US2008069784 discloses personal care compositions containing skin and/or hair care products. Such compositions are useful for regulating the condition of mammalian keratinous tissue in need of such treatments, particularly skin lightening.

WO9503779 and WO2006014237 describe cosmetic compositions which may contain alpha-bisabolol and salicylic acid.

Document PI0807326-0 claims a composition comprising alpha-bisabolol for improving a skin condition.

Document PI1010479 uses alpha-bisabolol in combination with other plant ingredients.

Thus, it is understood that in view of the state of the art found, the problem related to the need to provide cosmetic compositions to reduce and control skin oiliness as well as to reduce the pore sizes, maintain the skin pH and the natural and healthy skin microbiota still exists.

SUMMARY OF THE INVENTION

Thus, the present invention is intended to solve the technical issues of the state of the art by preparing a topical cosmetic composition.

In a first aspect, the present invention relates to a topical cosmetic composition in the form of a solution, which composition comprises salicylic acid, pyrrolidone carboxylic acid zinc salt (Zinc PCA) and *Candida saitoana* extract.

In a second aspect, the present invention relates to the use of the composition to reduce and control skin oiliness.

In a third aspect, the present invention relates to the use of the composition to reduce the average size of skin pores.

In a forth aspect, the present invention relates to the use of the composition to maintain the skin pH between 4.1 and 5.8.

In a fifth aspect the present invention relates to the use of the composition to reduce the porphyrin number of facial skin after 28 days of use of the composition of the first aspect.

Also, the inventive concept in common to all aspects of the invention is that they involve the composition of the first aspect.

From among the advantages of the present invention, in a non-exhaustive manner, are that it is able to:

eliminate the build up of impurities in the cells;

maintain physiological pH, helping to rebalance the microbiota;

prolonged oil control for up to 4 hours;

immediate reduction of shine and oiliness, removing up to 12.5% of oil immediately;

significantly reduce the average facial skin oiliness after 28 days of home use;

reduce the pore sizes;

These and other objects of the invention will be immediately valued by those skilled in the art and by companies with interest in the segment, and will be described in sufficient detail to be reproduced in the description below.

BRIEF DESCRIPTION OF THE FIGURES

In order to better define and clarify the present invention, the following figures are presented.

DETAILED DESCRIPTION OF THE INVENTION

Figure 1:
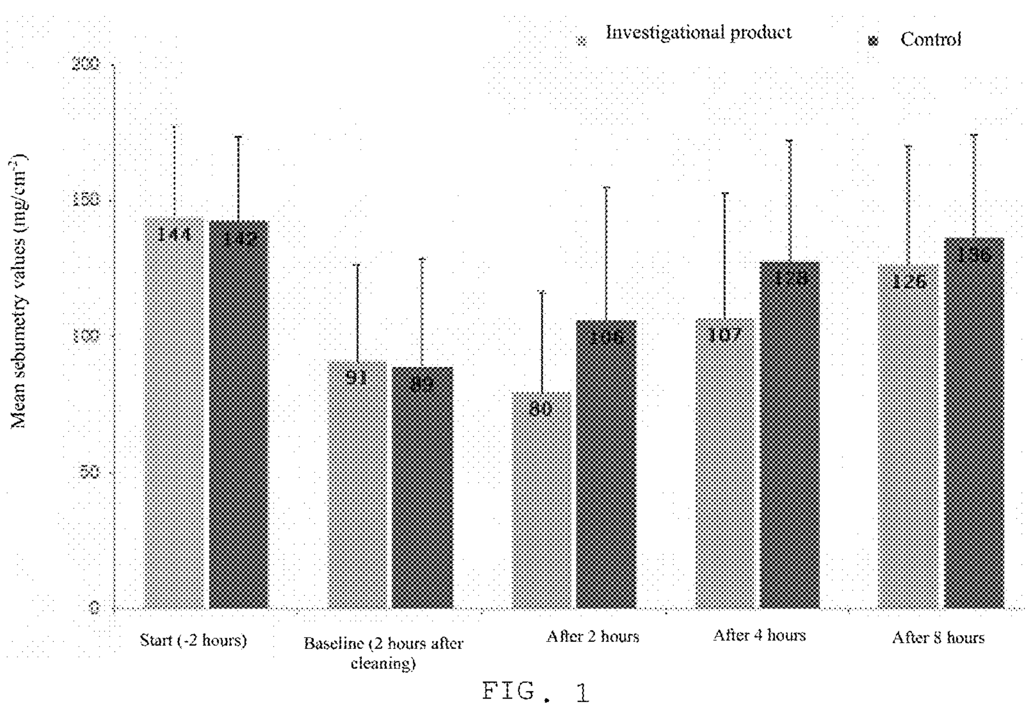
FIG. 1 graphically represents the mean values of sebaceous secretion obtained at the site of application of the facial tonic of the present invention and at the control site.

The present invention describes a topical cosmetic composition and uses thereof in reducing and controlling oiliness, reducing pores, maintaining the pH and the skin's physiological microbiota.

In the present invention, the term "maintenance of the skin microbiota" can also be understood as "preservation of the skin microbiota" or "microbiota balance", being defined as an ability to enable the presence of a natural and healthy skin microbiota. Furthermore, the term "skin microbiota" can also be understood as "skin flora".

In a first aspect, the present invention relates to a topical cosmetic composition in the form of a solution, which composition comprises salicylic acid, pyrrolidone carboxylic acid zinc salt (Zinc PCA) and *Candida saitoana* extract.

A solution is meant the cosmetic presented in a translucent form. Preferably, the cosmetic solution of the first aspect is a hydroalcoholic in the form of a tonic to be applied on the skin.

From among the required ingredients for the effects of the facial tonic are salicylic acid, pyrrolidone carboxylic acid zinc salt and *Candida saitoana* extract. Preferably, the composition comprises about 0.1 to 3% salicylic acid, about 0.2 to 2% pyrrolidone carboxylic acid zinc salt and about 0.1 to 3% *Candida saitoana* extract.

The hydroalcoholic solution containing the active ingredients provides the unclogging of pores, reduces oiliness and detoxifies the cells through mechanisms that prevent oxidation and residue build up.

Salicylic acid is a beta hydroxy acid (2-hydroxybenzoic acid). Salicylic acid acts as a keratolytic agent, cleaning clogged pores and preventing them from becoming clogged again. In addition, it acts in the reduction of dead cells and skin oil. Therefore, the compound promotes unclogging of pores and reduction in skin oiliness.

Zinc PCA or pyrrolidone carboxylic acid zinc salt is an ingredient that has an antimicrobial effect (inhibiting the lipase of acne-causing bacteria). In addition, the ingredient has a modulating effect on sebum secretion (decreasing the conversion of testosterone to dihydroxytestosterone by inactivating enzyme 5-alpha-reductase). PCA zinc reduces oiliness and the number of acne from comedones.

*Candida saitoana* extract is an active extracted by biotechnological fermentation of *Candida saitoana*, which is rich in alpha-glucans. The extract stimulates the cellular detoxification mechanism by autophagy—LC3-II marker in keratinocytes. It also acts on cellular and tissue protection against the build up of oxidation residues and protects against cell oxidation effects. It promotes an improvement in skin uniformity leaving it more radiant and healthier looking.

The combination of the ingredients of the first aspect makes it possible to maintain the skin physiological pH, helping to rebalance the skin microbiota. It also promotes immediate reduction and control of oiliness. Also, a progressive action in the reduction of sebum with continuous use is provided.

In one embodiment of the first aspect the invention further comprises cosmetically acceptable excipients. By cosmetically acceptable excipients is meant non-irritating and non-toxic substances, which are used to prepare and/or provide structure to a cosmetic form, and may or may not confer organoleptic properties on a composition such as, for example, color and odor, and may or may not provide a cosmetically desirable biological effect such as hydration. The cosmetically acceptable excipients of the present invention can be formulated in different amounts, depending on the type of characteristics envisioned in the final cosmetic product.

The cosmetically acceptable excipients in accordance with the present invention may be those known to the person skilled in the art, such as those cited in the "International Cosmetic Ingredient Dictionary & Handbook", 16th Edition.

In a particular embodiment, the cosmetically acceptable excipients of the present invention can be, in a non-exhaustive manner, those belonging to the classes of solvents, humectant, emulsifiers, emollients, preservatives, skin conditioners, skin protectors, denaturants, perfumes, antioxidants, chelating agents, dyes and buffers.

Preferably, the solvent comprises water, alcohol, dipropylene glycol, propylene glycol, or a mixture thereof; the humectant comprises glycerate phosphate (Glycerate-26), sorbitol, or a mixture thereof; the emulsifier comprises PPG-5-Ceteth-20, PEG-7 glyceryl cocoate, polysorbate 20, or a mixture thereof; the emollient comprises glycerin; the skin conditioner comprises panthenol, bisabolol, or a mixture thereof; the chelating agent comprises sodium glucolate; the buffer comprises sodium hydroxide.

The tonic of the present invention can be made by any process known to the person skilled in the art.

The composition of the first aspect is indicated for consumers having combined to oily skin and wish to complement their cosmetic treatment both in terms of cleaning and oil control, since the product prepares the skin for cosmetic treatment, toning it, maintaining the skin's normal pH, eliminating cellular toxins and reducing oiliness.

The methodology for using the composition is to apply it in the morning and at night after cleaning the skin. In addition, the product can be applied with a cotton pad on the face and neck. There is no need to rinse.

The hydroalcoholic solution comprising salicylic acid, zinc PCA and *Candida saitoanagera* extracts and the technical effects of the present invention differ from the state of the art.

The technique for assessing the reduction and control of oiliness is sebumetry, which has the benefit of being a non-invasive methodology that evaluates the sebaceous lipid secretion profile on the skin surface along a kinetics conceived as short or long.

As a result, the composition of the first aspect was found to reduce the skin's oiliness in an immediate and prolonged way. It also reduces the average facial skin oiliness after 28 days of use.

Thus, in a second aspect, the present invention relates to the use of the composition of the first aspect to reduce and control skin oiliness.

One embodiment of the second aspect of the invention relates to a prolonged reduction and control of skin oiliness.

In another embodiment the second aspect refers to the reduction and control of oiliness after 28 days of application of the product.

The effect of reducing the size/number of pores was achieved by a non-invasive methodology designated as image analysis, which evaluates the morphology and topographic characterization of the skin surface.

By the cited methodology, it was noted that there is an immediate reduction in the pore size by up to 7.2% and pores are apparently less visible by up to 90%.

Thus, in a third aspect the present invention relates to the use of the composition to reduce the average pore size of the skin.

The effect of skin pH maintenance was assessed using an objective non-invasive methodology designated as pHmetry, which assesses the amount of protonated entities in the form of H+ on the skin surface.

By the cited methodology, it was noticed that the physiological skin pH was maintained after using the product of the first aspect.

Thus, in a forth aspect, the present invention relates to the use of the composition to maintain the skin pH between 4.1 and 5.8.

A fifth aspect the present invention relates to the use of the composition to reduce the number of porphyrins of facial skin after 28 days of use of the composition of the first aspect.

The facial tonic of the present invention is applied to the skin with the aid of a cotton pad moistened with said tonic.

Examples—Embodiments

The examples shown herein are intended only to exemplify one of the numerous ways of carrying out the invention, without limiting its scope.

For the purpose of illustrating the technical effects of the present invention, and not to limit it, whenever the examples refer to an "investigational product" reference will be made to a topical cosmetic composition in the form of a facial tonic, which is a preferred embodiment of the composition of the first aspect. The composition of the "investigational product" can be found in table 1.

TABLE 1

Composition of the investigational product (tonic)

| Ingredient | Concentration (% w/w) |
|---|---|
| Water | 65.08 |
| Ethyl alcohol | 15.00 |
| Propylene glycol | 5.00 |
| Glycerate | 3.00 |
| PPG-5-Ceteth-20 | 2.50 |
| PEG-7 Glyceryl Cocoate | 2.00 |
| Glycerin | 2.00 |
| Polysorbate 20 | 1.00 |
| Salicylic acid | 0.50 |
| Benzilic alcohol | 1.00 |
| PCA zinc | 0.75 |
| *Candida saitoana* extract. | 0.75 |
| panthenol | 0.50 |
| Bisabolol | 0.50 |
| Perfume | 0.2 |

Example 1—Effect of the Investigational Product on the Reduction and Control of Facial Skin Oiliness after Application of a Cosmetic Product Goal This example is intended to demonstrate the effect of the investigational product on the reduction and control of skin oiliness at 2, 4 and 8 hours after application.

Methodology

Twenty participants with a mean age of 45±7 years were selected. Among the participants, the phototype (Fitzpatrick) distribution was as follows: 70% phototype III and 30% phototype IV. Participants were instructed to discontinue the use of any cosmetic products on the face 72 hours prior to the start of the study.

In the frontal region (forehead) of the participants, two sites were marked (areas measuring 2.5 cm×4.0 cm). After 30 minutes of the participant staying in an air-conditioned environment, the initial data on oiliness was obtained at the marked sites.

Then, the procedure of cleaning the sites with water and neutral soap was performed. After 2 hours of cleaning, new measurements of skin oiliness were performed to collect baseline oiliness values. After these 2 hours the investigational product was applied and new measurements of skin oiliness were obtained after 2, 4 and 8 hours of application of the product.

The investigational product was applied to the participants with the aid of a cotton pad. The cotton pad was moistened with 1 mL of the investigational product, and the same was passed over the site 3 times in the same direction, keeping the pressure and speed constant.

Measurements were made by placing a probe to measure the oil content by means of a photometric method (using Cassette Sebumeter SM810), keeping the pressure constant for 30 seconds. Reduction in skin oiliness is evidenced by the decreased amount of sebaceous secretion, the lower the value, the greater the reduction in oiliness, and the longer this reduction lasts, the greater the control of oiliness provided.

Results

As a result, the investigational product was found to provide a significant reduction in easy skin oiliness after 2 hours of application, relative to the baseline condition (2 hours after cleaning the site with water and neutral soap). It shows that the investigational product reduced facial skin oiliness for up to 2 hours.

The investigational product was shown to provide a significant reduction in easy skin oiliness after 4 hours of application as compared to control (skin with no other product applied). It shows that the investigational product reduced facial skin oiliness for up to 4 hours.

The investigational product was shown to provide a significant mean reduction in facial skin oiliness relative to the baseline condition of 12.5% after 2 hours of application.

The graph in FIG. 1 illustrates the values found in example 1.

Example 2—Effect of the Investigational Product on the Reduction of Facial Skin Oiliness after 28 Days of Home Use Objective The instant example is intended to demonstrate the reduction in facial skin oiliness after 28 days of home use of the investigational product.

Methodology

Twenty-three participants with a mean age of 44±7 years were selected. Among the participants, the phototype (Fitzpatrick) distribution was as follows: 4% phototype II, 70% phototype III and 26% phototype IV. Participants were instructed to discontinue the use of any cosmetic products on the face 72 hours prior to the start of the study.

Facial skin oiliness measurements were performed in the forehead region of the research participants at the beginning of the study and after 28 days of home use of the investigational product. Measurements were obtained after the participants had remained at rest for 30 minutes in a controlled environment.

Participants were instructed to apply the product with the aid of a cotton pad on the face and neck in the morning and at night.

Results

There was a significant reduction in facial skin oiliness after 28 days of home use of the investigational product. A significant mean reduction in facial skin oiliness being of 33.7% after 28 days of home use.

Figure 2:
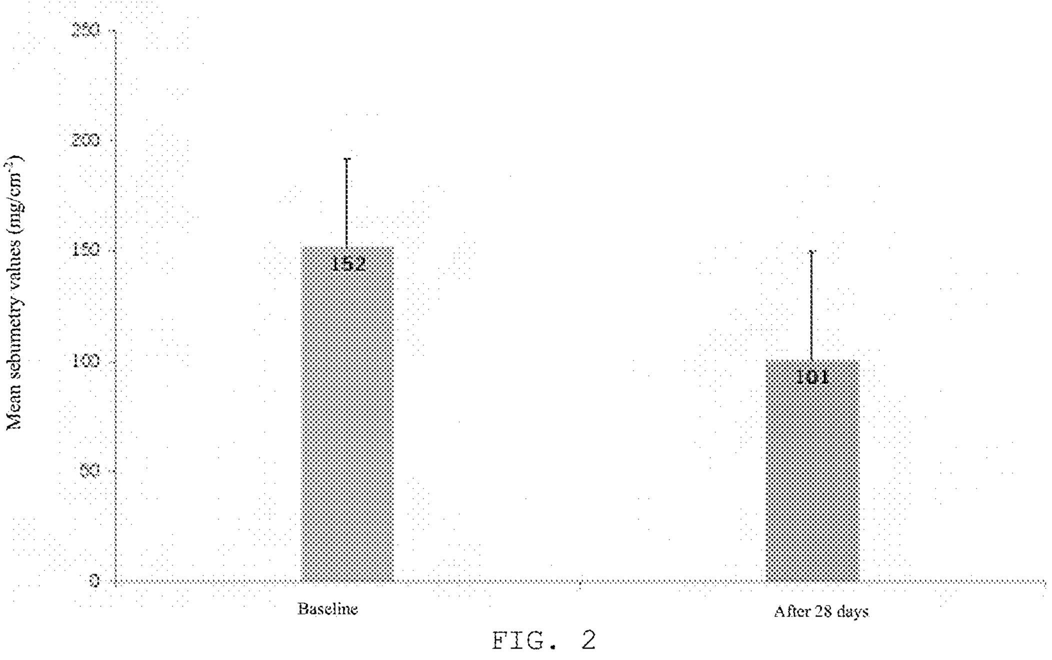
FIG. 2 depicts sebaceous secretion values obtained after 28 days of use of the facial tonic of the present invention.

FIG. 2 represents the results achieved in this example.

Example 3—Assessment of the Product on the Reduction of Facial Skin Pore Size by Image Analysis This example is intended to demonstrate the effect of the investigational product on the issue of the reduction in pore size after 15 minutes, 2, 4 and 8 hours of application of the product.

Methodology

Twenty participants with a mean age of 45±7 were selected. Among the participants, the phototype (Fitzpatrick) distribution was as follows: 70% phototype III and 30% phototype IV. Participants were instructed to discontinue the use of any cosmetic products on the face 72 hours prior to the start of the study. There were no reports or evidence of adverse reactions during the study.

The methodology consisted of assessing the reduction in the pore average size in the facial skin of the research participants through image analysis.

The results achieved are a comparison between high resolution photographic images under controlled and standardized conditions. Data were obtained at an initial time (prior to application of the product) and 15 minutes, 2, 4 and 8 hours after application of the mask.

According to each volunteer's face morphology, a selection area was determined for analysis of the apparent pore average size. Analysis was kept constant for each participant in terms of size and placement between the evaluation conditions, thus allowing a comparison to be made between the images.

Figure 4:
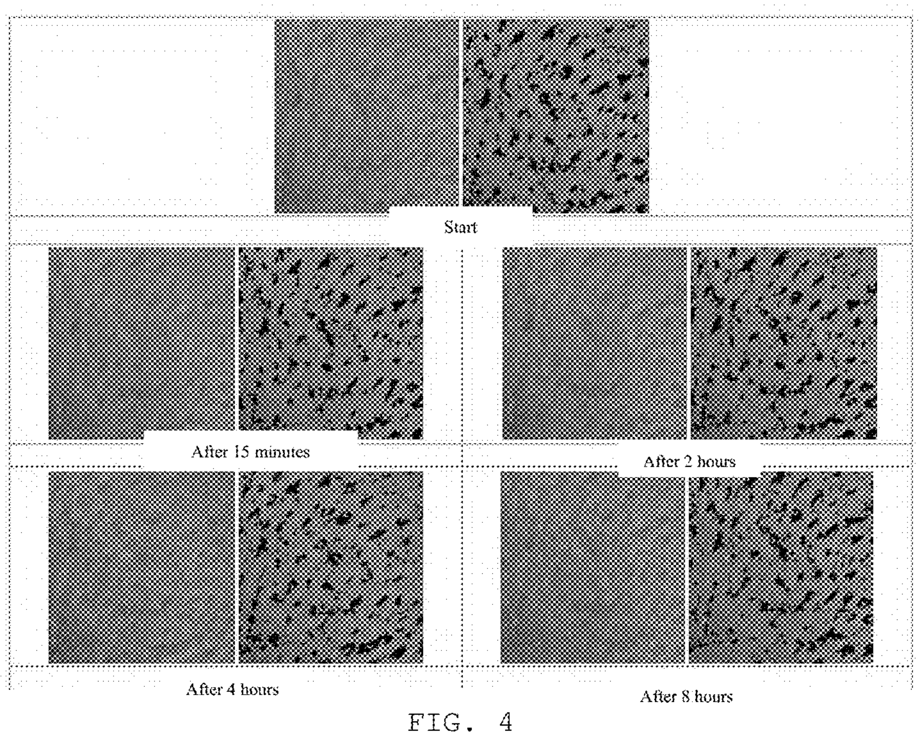
FIG. 4 represents examples of images obtained for one of the research participants at the beginning of the study, after 15 minutes 2, 4 and 8 hours of application of the facial tonic of the present invention.

The selected areas were assessed using a particle morphology analysis tool, which identifies, isolates and analyzes via color contrasting information the geometric parameters of the detected visible pores, as shown in FIG. 4.

Results

After 15 minutes of application of the investigational product, there was a significant reduction in the average pore size of 5.2, reaching up to 7.2%. After 2 hours of application of the investigational product, there was a significant reduction in the average pore size of 4.2%, reaching up to 5.5%. After 4 hours of application of the investigational product, there was a significant reduction in the average pore size of 2.0%, reaching up to 3.6%. After 8 hours of application of the investigational product, there was no significant difference in the average pore size relative to the baseline condition.

Figure 3:
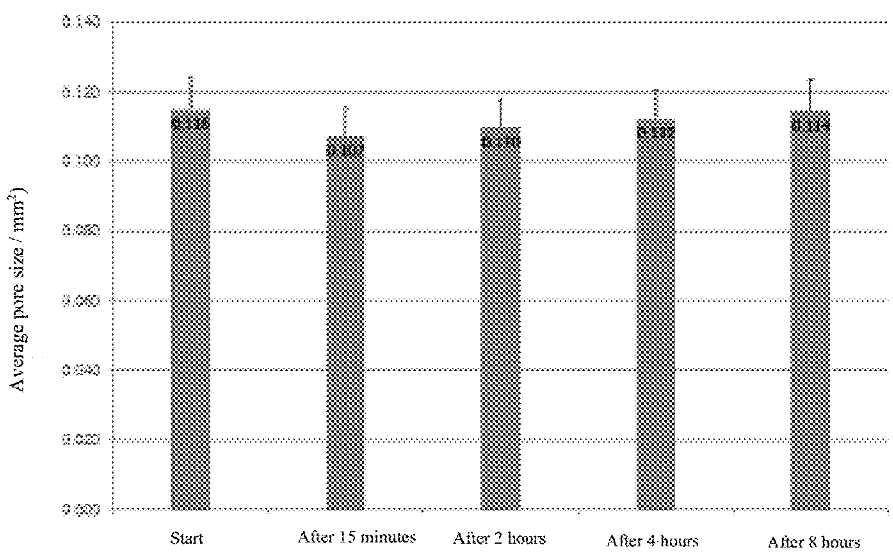
FIG. 3 graphically represents the average values of the average pore sizes of the research participants after 15 minutes, 2, 4 and 8 hours of application of the facial tonic of the present invention.

FIG. 3 represents the results achieved in this study.

Example 4—Instrumental Assessment of Skin pH after Application of an Investigational Product Twenty-one participants with a mean age of 19 to 59 years were selected for the study. The participants were instructed to discontinue the use of any topical product.

Two symmetrical 10 $cm^2$ areas were demarcated in the anterior region of the participants' forearms. One area was used for product application and the other one was kept as a control (untreated area), randomly. Assessments were made using the Seven 2 Go Mettler Toledo S8 portable pH meter equipment prior to application of the product and after 30, 60 and 90 minutes of application.

Results

As a result, the investigational product was found to maintain the average pH at the analysis times, with values between the range of 4.1 and 5.8.

Figure 5:
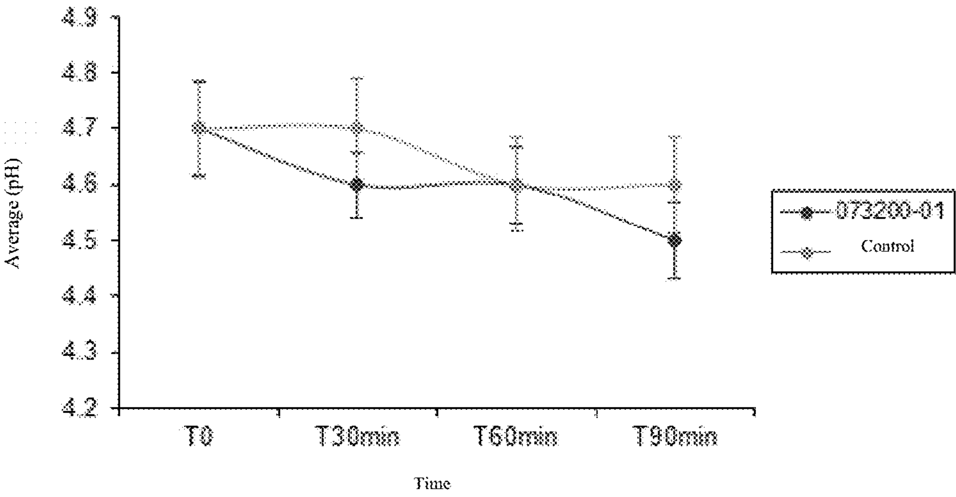
FIG. 5 represents the average pH values over time with the use of the facial tonic of the present invention in relation to the control group.
Figure 6:
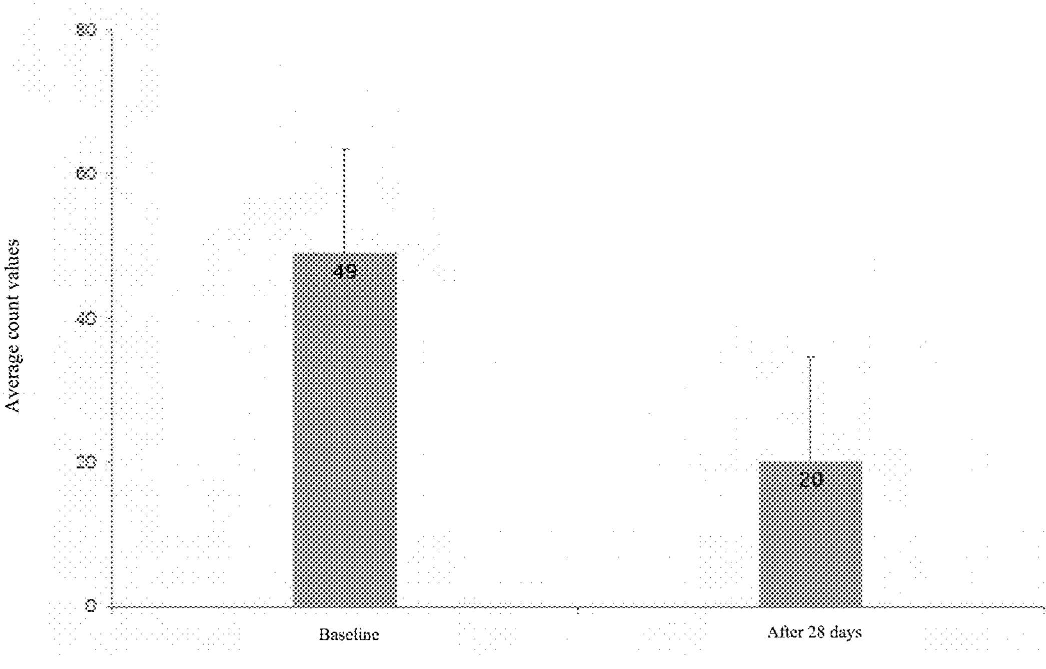
FIG. 6 graphically illustrates the mean porphyrin count values obtained at baseline and after 28 days of treatment with the facial tonic of the present invention.

FIG. 5 represents the values obtained in example 3, which is a comparison with the control group.

Example 5—Instrumental Assessment in the Maintenance of Skin Microbiota

The study was intended to assess the maintenance of skin flora provided by the use of the investigational product by counting porphyrins on the facial skin.

Twenty-three participants with a mean age of 44±7 years were included in the study. The phototype (Fitzpatrick) distribution was as follows: 4% phototype II, 70% phototype III and 26% phototype IV. Participants were instructed to discontinue the use of any cosmetic products on the face 72 hours prior to the start of the study. There were no reports or evidence of adverse reactions during the study.

The methodology consisted of obtaining photographic images of the face of the research participants at the beginning of the study and after 28 days of treatment. By assessing the images obtained, parameters can be calculated, which show the numerical variations of porphyrins.

The participants were instructed to apply the product in the morning and at night, after cleaning the skin, applying the product with a cotton pad over the face and neck.

As a result, after 28 days of home use of the investigational product, there was a significant reduction in the number of porphyrins on the facial skin. It shows that the investigational product helps balance the oily skin microflora.

Those skilled in the art will value the knowledge presented herein and may reproduce the invention in the disclosed embodiments and other variants, as covered by the scope of the appended claims.

The invention claimed is:

1. A topical cosmetic composition characterized by consisting of from 0.1 to 3% salicylic acid, 0.2 to 2% pyrrolidone carboxylic acid zinc salt, and 0.1 to 3% *Candida saitoana* extract, and one or more cosmetically acceptable excipients;

wherein the cosmetically acceptable excipients are selected from the class of: solvents, humectants, emulsifiers, emollients, preservatives, skin conditioners, skin protectors, denaturing agents, perfumes, antioxidants, chelating agents, dyes and buffers.

2. The composition according to claim 1, characterized in that it is a hydroalcoholic composition.

3. The composition according to claim 1, characterized in that it comprises i) a solvent comprising water, alcohol, dipropylene glycol, propylene glycol, or a mixture thereof;

ii) a humectant comprising glycerate phosphate, sorbitol, or a mixture thereof;

iii) an emulsifier comprising PPG-5-Ceteth-20, PEG-7 glyceryl cocoate, polysorbate 20, or a mixture thereof;

iv) an emollient comprising glycerin;

v) a skin conditioner comprising panthenol, bisabolol, or a mixture thereof;

vi) a chelating agent comprising sodium glucolate; and vii) a buffer comprising sodium hydroxide.

4. The composition according to claim 1, characterized in that it is a tonic.

5. A tonic for facial application, characterized in that it comprises the composition as defined in claim 1.

* * * * *